US00PP33235P2

(12) United States Plant Patent
Arts

(10) Patent No.: US PP33,235 P2
(45) Date of Patent: Jul. 6, 2021

(54) ***DIANTHUS* 'DDTOW14-0'**

(50) Latin Name: ***Dianthus* hybrid**
Varietal Denomination: DDTOW14-0

(71) Applicant: Agriom Trade BV, de Kwakel (NL)

(72) Inventor: Niels Arts, Aalsmeer (NL)

(73) Assignee: Agriom Trade B.V.

( * ) Notice: Subject to any disclaimer, the term of this patent is extended or adjusted under 35 U.S.C. 154(b) by 0 days.

(21) Appl. No.: 17/060,019

(22) Filed: Sep. 30, 2020

(51) Int. Cl.
*A01H 6/30* (2018.01)
*A01H 5/02* (2018.01)

(52) U.S. Cl.
USPC ..... Plt./273

(58) Field of Classification Search
USPC ..... Plt./273
See application file for complete search history.

*Primary Examiner* — Annette H Para
(74) *Attorney, Agent, or Firm* — Cassandra Bright

(57) ABSTRACT

A new and distinct variety of *Dianthus* plant named 'DDTOW14-0' is disclosed, characterized by unique bi-color flowers of salmon with well-defined white margins. Plants bloom for an extended period into the Summer and are hardy to USDA Zone 5. The new variety is a *Dianthus*, typically produced as a garden or container plant.

2 Drawing Sheets

Figure 1:
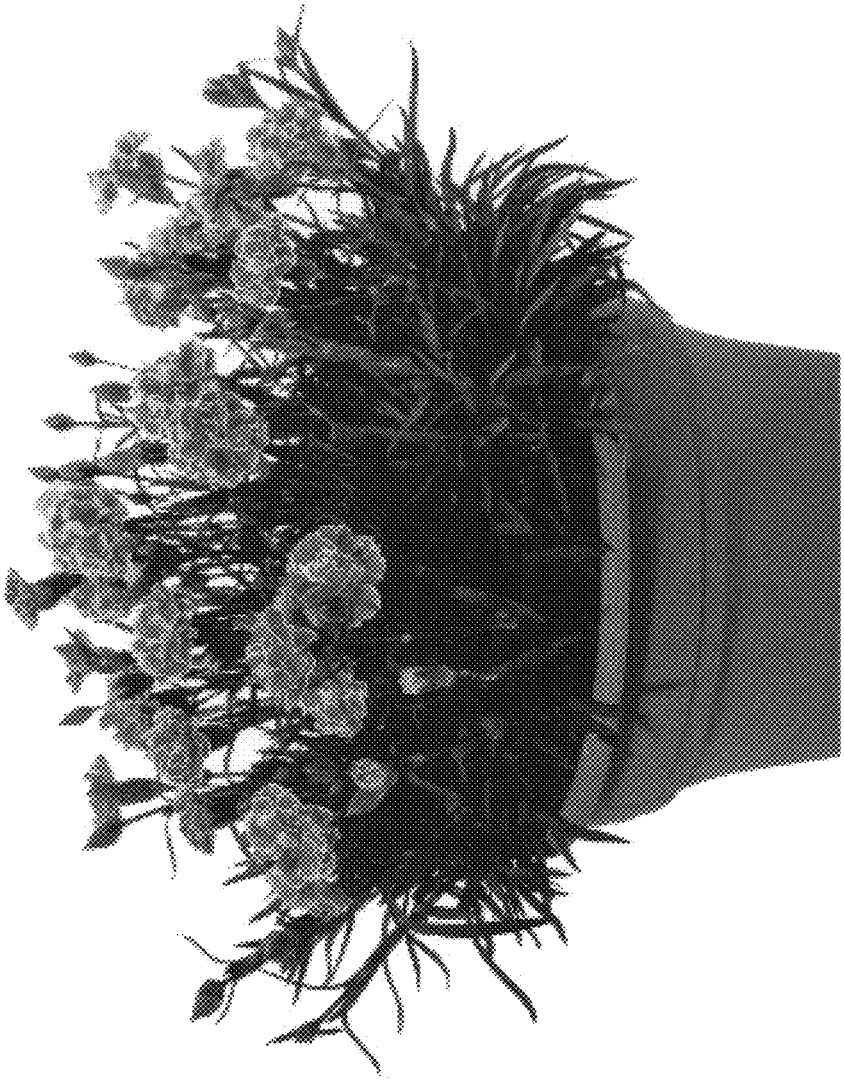

Latin name of the genus and species: *Dianthus* hybrid.
Variety denomination: 'DDTOW14-0'.

BACKGROUND OF THE INVENTION

The new cultivar is a product of a planned breeding program. The new variety originated as the result of the crossing of the female parent, an unpatented, proprietary *Dianthus* referred to as '13-307-001'. and the pollen parent, a different unpatented proprietary *Dianthus* referred to as '13-130-002'. The crossing was made during July 2016 at a commercial greenhouse in Santa Paula, Calif. 'DDTRO15-0' was discovered and selected at a commercial greenhouse in Santa Paula, Calif., in July of 2017.

Asexual reproduction of the new cultivar 'DDTOW14-0' was first performed in Santa Paula, Calif. at a research greenhouse by vegetative terminal cuttings in April of 2018. 'DDTOW14-0' has since produced several generations and has shown that the unique features of this cultivar are stable and reproduced true to type.

SUMMARY OF THE INVENTION

The cultivar 'DDTOW14-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDTOW14-0'. These characteristics in combination distinguish 'DDTOW14-0' as a new and distinct *Dianthus* cultivar:

1. Unique deep salmon colored flowers with a distinct white margin on the petals.
2. Day-length neutral flowering.
3. Suitability for both garden and container uses.

4. Extended bloom time into Summer and Fall months.
5. Hardy to USDA Zone 5.

PARENTAL COMPARISON

Plants of the new cultivar 'DDTOW14-0' are comparable to the seed parent in most horticultural characteristics; however, the new variety 'DDTOW14-0' differs in the following:

1. Plants of the new variety are more compact than plants of the seed parent.

Plants of the new cultivar 'DDTOW14-0' are comparable to the pollen parent in most horticultural characteristics; however, the new variety 'DDTOW14-0' differs in the following:

1. The new variety produces multi-whorled flowers, the pollen parent produces single flowers.

COMMERCIAL COMPARISON

Plants of the new cultivar 'DDTOW14-0' are comparable to the commercial *Dianthus* variety 'DDTHP02-0', U.S. Plant Pat. No. 28,102. The two *Dianthus* varieties are similar in most horticultural characteristics; however, the new variety 'DDTOW14-0' differs in the following:

1. The new variety produces bi-color salmon and white flowers while this comparator has solid pink flowers.
2. Foliage of the new variety is brighter green than foliage of this comparator.

Plants of the new cultivar 'DDTOW14-0' are comparable to the commercial *Dianthus* variety 'DCACR08-0', U.S. Plant Pat. No. 30,026. The two *Dianthus* varieties are similar in most horticultural characteristics; however, the new variety 'DDTOW14-0' differs in the following:

1. The new variety produces bi-color salmon and white flowers while this comparator has solid dark pink flowers.
2. Foliage of the new variety is brighter green than foliage of this comparator.

BRIEF DESCRIPTION OF THE PHOTOGRAPHS

The accompanying photograph in FIG. 1 illustrates in full color a typical plant of 'DDTOW14-0' in a greenhouse in Santa Paula, Calif. This plant are approximately 12 weeks old, grown in a 6 inch pot.

Figure 2:
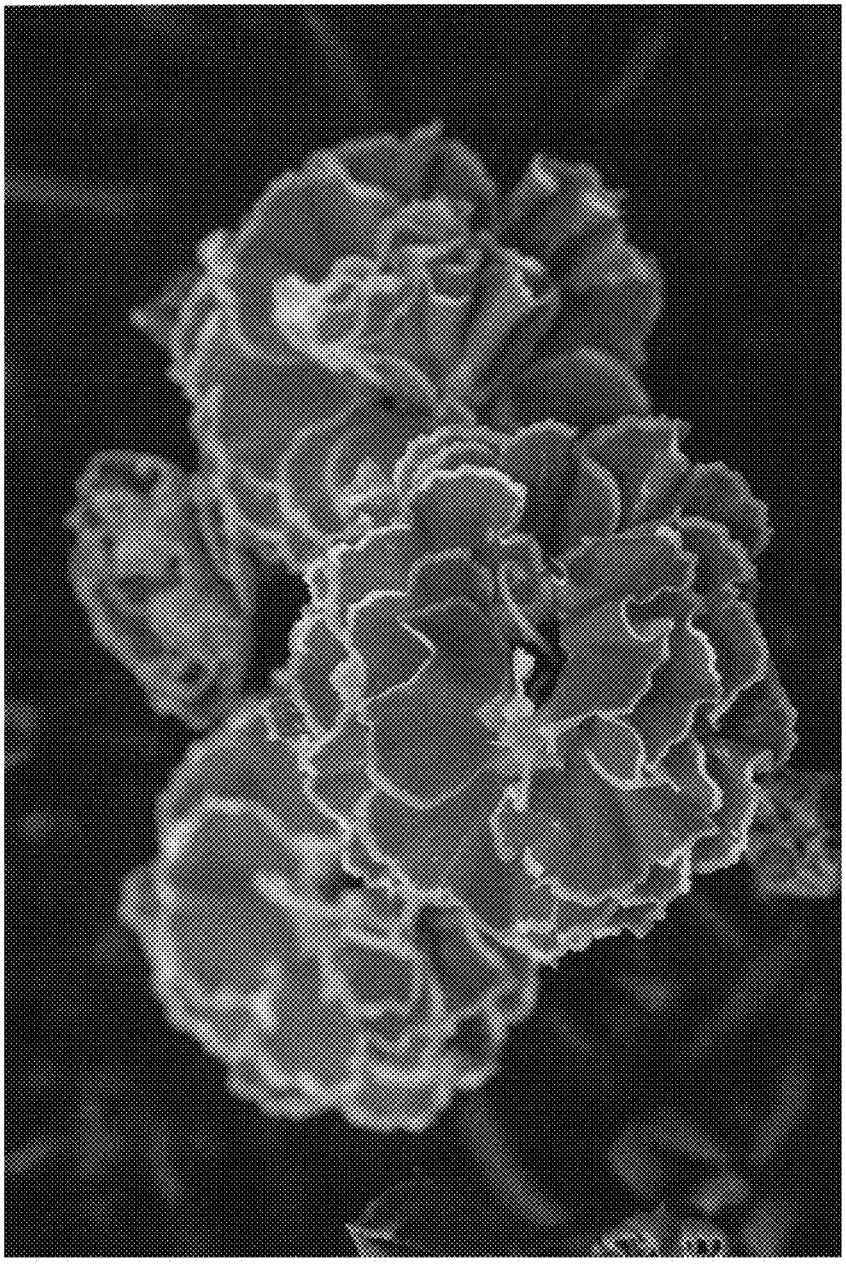

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DDTOW14-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus* hybrid 'DDTOW14-0'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near Orange-White 159C.

PLANT

Age of plant described: Approximately 20 weeks from rooted cutting.

Pot size: 6 inches.

Plant type: Compact upright flowering perennial.

Plant habit: Upright growing stems emerge basally.

Plant spread: Approximately 30 cm.

Height: Approximately 22 cm to top of flowering plane. Approximately 16 cm to top of foliar plane.

Length plant stem: Average range 7 to 13 cm.

Diameter of plant stem: Approximately 3 mm.

Quantity stems: Approximately 30.

Stem:

*Color*.—Near RHS Green N138B.

*Texture*.—Smooth.

Internode length: 2.2 to 3.8 cm.

FOLIAGE

Leaf:

*Arrangement*.—Opposite (in pairs).

*Quantity*.—Approximately 12 fully expanded per stem.

*Average length*.—4.5 to 7.0 cm.

*Average width*.—5 mm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near RHS Green 137C. Young foliage under side: Near RHS Green 138A. Mature foliage upper side: Near RHS Green 137A. Mature foliage under side: Near RHS Green 137B.

*Venation*.—Type: Linear. Venation color upper side: Indistinguishable from foliage. Venation color under side: Indistinguishable from foliage.

FLOWER

Natural flowering season: Continuous flowering from Spring until Fall.

Inflorescence type and habit: Umbel of 2 to 4 flowers.

Flower longevity on plant: 2-3 weeks.

Quantity of flowers: Approximately 30 to 40 flowers on a 12 week old plant.

Flowers persistent or self cleaning: Persistent.

Fragrance: Very mild sweet, clove-like scent.

Inflorescence (umbel) size:

*Diameter*.—Approximately 6.5 cm.

*Height*.—Approximately 6.0 cm.

Individual flower size:

*Diameter*.—Approximately 3.9 cm.

*Length*.—Approximately 3.4 cm.

Petals:

*Petal arrangement*.—Multiple whorl.

*Shape*.—Spatulate.

*Base*.—Attenuate.

*Margin*.—Serrated.

*Apex*.—Serrated.

*Length*.—2.0 cm.

*Width*.—1.5 cm.

*Petal quantity*.—Average range 15 to 20.

*Texture*.—Smooth all surfaces.

*Aspect*.—Reflexed back.

Color:

*When opening*.—Upper surface: Near RHS Red-46B. Well defined margin White N155C. Base Yellow-Green 145C. Lower surface: Near RHS Red 36B. Upper petal flushed 46C. Base Red 36D flushed Yellow-Green 145D.

*Fully opened*.—Upper surface: Near RHS Red 45D. Well defined margin White N155C. Center line White N155C. Lower surface: RHS Red 56B. base Yellow-Green 145D.

*Fading*.—Upper surface: Near RHS Red 50B. Well defined margin White N155C. Center line White N155C. Lower surface: RHS Red 56B. base Yellow-Green 145D.

Tube:

*General description*.—Tube consists of the elongated, unfused base of the petals. Tube shape caused by a fused calyx.

*Length*.—1.9 cm.

*Width*.—0.8 cm.

*Texture*.—Smooth.

Color:

*Fully opened*.—Inner surface: Near RHS Green 137B. Outer surface: Near RHS Green 137B.

Bud:

*Shape*.—Elongated cylinder.

*Length*.—Average 2.0 cm.

*Diameter*.—Average 1.0 cm.
*Color*.—Appearing petals colored near Red 53A.

Sepals:
*Quantity*.—5.
*Arrangement*.—Fused tube.
*Shape*.—Cylindric.
*Length*.—1.7 cm.
*Width*.—0.4 cm.
*Margin*.—Entire.
*Apex*.—Acute.
*Texture*.—Smooth upper and lower surfaces.
*Color*.—Near RHS Green 137B.

Bracteoles:
*Shape*.—Narrow Deltoid.
*Quantity per flower*.—5-7.
*Length*.—Approximately 5 to 7 mm.
*Width*.—Approximately 3 to 4 mm.
*Margin*.—Entire.
*Texture*.—Smooth.
*Color*.—Near RHS Green 137B.

Peduncle:
*Length*.—Average 2.6 cm.
*Diameter*.—2.0 mm.
*Color*.—Near RHS Green 137A.
*Orientation*.—Upright.
*Strength*.—Moderate.
*Texture*.—Smooth.

REPRODUCTIVE ORGANS

Stamens:
*Number*.—6.
*Filament*.—Length: 1.1 cm. Color: RHS White N155B.
*Anthers*.—Shape: Oblong. Length: 2 mm. Color: RHS Green-Yellow 1D. Pollen: Not observed.

Pistil:
*Number*.—1.
*Length*.—Approximately 2.8 cm.
*Style*.—Number: 2. Length: Approximately 2.1 cm. Color: Near RHS White N155B.
*Stigma*.—Length: about 0.5 mm. Shape: Linear, arching. Color: Near RHS White N155B.
*Ovary*.—Shape: Oblong. Diameter: 0.4 cm. Length: 0.7 cm. Color: Near RHS Yellow-Green N144D.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.

Temperature tolerance: USDA zones 5 through 10 tolerant.

What is claimed is:

1. A new and distinct cultivar of *Dianthus* plant named 'DDTOW14-0' as herein illustrated and described.

* * * * *